United States Patent [19]
Becherer et al.

[11] Patent Number: 6,028,192
[45] Date of Patent: Feb. 22, 2000

[54] PROCESS FOR THE PREPARATION OF DIACYLIMIDES

[75] Inventors: Johannes Becherer, Maintal; Klaus Delpy, Dietzenbach; Karl-Heinz Keil, Hanau; Bernhard Mees, Eppstein, all of Germany

[73] Assignee: Clariant GmbH, Frankfurt, Germany

[21] Appl. No.: 09/013,756

[22] Filed: Jan. 27, 1998

[30] Foreign Application Priority Data

Jan. 31, 1997 [DE] Germany .............. 197 03 549

[51] Int. Cl.[7] .............. C07D 205/08; C07D 223/10; C07D 211/22; C07D 295/00; C07C 233/00
[52] U.S. Cl. .............. 540/200; 540/362; 540/451; 540/529; 546/221; 546/245; 548/530; 548/539; 548/540; 564/152; 564/155; 564/159
[58] Field of Search .............. 564/152, 155, 564/159; 540/200, 362, 451, 529; 546/221, 245; 548/530, 539, 540

[56] References Cited

FOREIGN PATENT DOCUMENTS 0 617 018   9/1994   European Pat. Off. .
WO 91/15474  10/1991  WIPO .

OTHER PUBLICATIONS

Elsevier Science Ltd., PII: S0040–4039(96)02417–3, Mekonnen and Ziffer, A New Route to N–Substituted 11–Azaartemisinins, 1997.

XP–002082623, H. Sasaki et al.: "Synthesis and anticonvulsant activity of 1–acyl–2–pyrrolidinone derivatives" *Journal of Medicinal Chemistry*, Bd. 34, Nr. 2, 1991, pp. 628–633.

XP–002082624, M. Bodanszky et al.: "Side reactions in peptide synthesis. II. Formation of succinimide derivatives from aspartyl residues" *Journal of Organic Chemistry*, Bd. 40, Nr. 17, 1975, pp. 2495–2499.

XP002082625, T. Tsunoda et al.: "An efficient method for hydrolysis of N–monosubstituted amides via acetoxypivalimides" *Tetrahedron Letters*, Bd. 31, Nr. 5, 1990, pp. 731–734.

XP–002082626, F.M.F. Chen et al.: "Diisopropylamine eliminates dipeptide formation during the acylation of amino acids using benzoyl chloride and some alkyl chloroformates" *Canadian Journal of Chemistry*, Bd. 65, 1987, pp. 1224–1227.

*Primary Examiner*—Mukund J. Shah
*Assistant Examiner*—Brenda Coleman
*Attorney, Agent, or Firm*—Miles B. Dearth

[57] ABSTRACT

The present invention relates to a process for the preparation of compounds of the formula 1

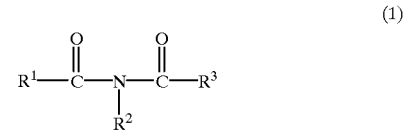

(1)

by reacting a secondary acid amide of the formula 2

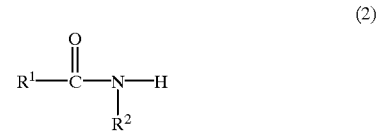

(2)

with an acid chloride of the formula 3

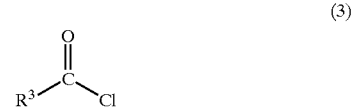

(3)

in the presence of N,N-diisopropyl-N-ethylamine. $R^1$, $R^2$ and $R^3$ are alkyl or alkenyl radicals, if required also aryl radicals. The compounds of the formula 1 are suitable for use as insecticides or bleach activators.

11 Claims, No Drawings

PROCESS FOR THE PREPARATION OF DIACYLIMIDES

The present invention relates to a process for the preparation of diacylimides from acid amides and acid chlorides in the presence of N,N-diisopropyl-N-ethylamine.

EP-A-0 523 085 discloses the two-stage reaction of 3-dimethylaminopropyamine with acetic anhydride to give N,N-diacetyldimethylaminopropylamine. Whilst this reaction is successful in the case of symmetrical diacetylimides, it is unsuccessful for the preparation of asymmetrical diacetylimides since it leads to transacetylation and thus to undesired symmetrical compounds.

The use of acid chlorides as starting materials is known in the literature. Thus, in the reaction known as the Schotten-Baumann reaction, an amide is acylated using an acid chloride in the presence of a base, such as NaOH or soda, in water. The base is needed to bind the hydrochloric acid produced. The disadvantage of this reaction is the fact that the yield of the desired target product can be very low for products which are sensitive to hydrolysis.

Tetrahedron Letters 31 (5), 731-734, 1990, discloses the reaction of acid chlorides with secondary amides in the presence of triethylamine. Although the yield is given as above 90%, the work-up of triethylamine is unsatisfactory from ecological and economic viewpoints. The triethylammonium hydrochloride formed must be decomposed using an inorganic base (e.g. aqueous sodium hydroxide solution) after the reaction to recover triethylamine. Because of the good mutual solubility of triethylamine and water, it is necessary to carry out involved distillative separation of the two components, but this nevertheless fails to prevent a relatively high concentration of triethylamine in the waste water.

The object of the present invention is, therefore, to provide a process in which secondary acid amides are reacted selectively and in high yields with acid chlorides in the presence of a base which can be regenerated again without impact on the environment and without excessive costs.

Surprisingly, it has been found that this object can be achieved by the use of N,N-diisopropyl-N-ethylamine (so called Hünig base).

The invention provides a process for the preparation of compounds of the formula 1

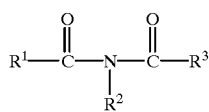

(1)

where $R^1$ and $R^2$ are $C_1$–$C_{24}$-alkyl or $C_2$–$C_{24}$-alkenyl, or where $R^1$ and $R^2$ form a ring having 4 to 8 carbon atoms, and $R^3$ is $C_1$–$C_{24}$-alkyl, $C_2$–$C_{24}$-alkenyl or aryl, which comprises reacting a secondary acid amide of the formula 2

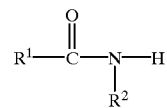

(2)

with at least one acid chloride of the formula 3

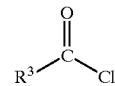

(3)

in the presence of N,N-diisopropyl-N-ethylamine.

If $R^1$ and $R^2$ form a ring, this may then be substituted by an $R^4$ radical, as shown in formula 4:

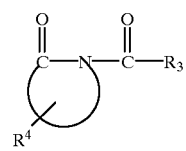

(4)

$R^4$ can be $C_1$–$C_4$-alkyl or $C_2$–$C_4$-alkenyl.

$R^1$ and $R^2$ can independently of one another be linear or branched. $R^1$ and $R^2$ are preferably $C_1$–$C_{10}$-alkyl or $C_2$–$C_{10}$-alkenyl, in particular $C_8$–$C_{10}$-alkyl or $C_8$–$C_{10}$-alkenyl, and $R^2$ is also particularly preferably methyl. If $R^1$ and $R^2$ form a ring, a ring containing 7 atoms is preferred, which means that $R^1$ and $R^2$ together have 5 carbon atoms.

$R^3$ can be linear or branched. $R^3$ is preferably $C_1$–$C_{12}$-alkyl, $C_6$–$C_{14}$-aryl or $C_6$–$C_{14}$-aralkyl, in particular benzyl or toluyl.

The reaction can either be carried out using suitable solvents, such as toluene, xylene and/or tetralin, or, preferably, without solvents. Both the acid chloride and the N,N-diisopropyl-N-ethylamine are used in a molar excess of in each case up to 10% by weight, based on the secondary amide.

The order in which the starting materials are added is arbitrary; preferably, the secondary amide is introduced initially and the acid chloride and the base are simultaneously added dropwise at the required reaction temperature. The reaction temperature is usually between 25 and 150° C., preferably between 80 and 130° C.

When the reaction is complete, the diacylimide is purified by adding sufficient water for the Hünig base hydrochloride formed to dissolve and for the imide to be separated off by phase separation or filtration. The resulting diacylimide may be subjected, if required, to further purification steps (such as distillation or crystallization). The aqueous Hünig base hydrochloride solution is then admixed with an equimolar quantity of NaOH, and the Hünig base separates out as the upper phase and can be separated from the lower aqueous phase following phase separation. The amount of residual water in the Hünig base is less than 0.15%. This is surprising since the structurally-related triethylamine is miscible with water to an almost unlimited extent. The resulting base can be reused either directly or after any purification that may be necessary (e.g. distillation).

Diacylamides of the described type can, for example, be used as insecticides or bleach activators.

EXAMPLE 1

In a 4 l multinecked flask fitted with stirrer, thermometer, gas inlet pipe, reflux condenser and 2 dropping funnels, 1370.3 g (8 mol) of N-methylpelargonamide (m.p. about 37° C.) are blanketed with nitrogen and melted. At an internal temperature of 85–95° C., 690.8 g (8.8 mol) of acetyl chloride and 1116.7 g (8.64 mol) of Hünig base are added dropwise from two parallel dropping funnels over the course of 70 minutes at such a rate that the acetyl chloride is added to the mixture about 10–20% more quickly than the Hujnig base. The reaction is cooled throughout using a water bath. When addition is complete, the mixture is then stirred for 4 hours at 85–90° C., giving brown, readily stirrable suspension of Hünig base hydrochloride in the crude product. This suspension is cooled to room temperature with stirring. Some of the hydrochloride sticks to the upper part of the flask wall. The mixture is admixed with 1262 ml of water and stirred vigorously for half an hour, the Hünig base hydrochloride dissolving completely. The mixture is allowed to settle (for about half an hour) and the lower, cleanly separated aqueous phase is withdrawn with suction. The mixture is admixed with a further 800 ml of water, vigorously stirred and transferred to a separating funnel for better separation. The mixture is allowed to settle for about 1.5 hours and the cleanly separated lower aqueous phase is run off. The organic product phase is transferred into a 2 l three-necked flask fitted with stirrer and internal thermometer and distilled at 5 to 7 mbar without reflux via a 10 cm packed column with 6 mm Raschig rings. Firstly, forerunnings are removed at a head temperature of 30 to 130° C., then the product is distilled off at a head temperature of 135 to 143° C. Throughout most of the distillation, the oilbath temperature is about 155° C., at the end the bath temperature is raised to 210° C. and distillation is carried out until nothing else passes over. The distillation residue has low viscosity even after cooling to room temperature. The product yield is 94% and the resulting N-nonanyl-N-acetylmethylimide has a purity of 99%.

Recovery of the Hünig base

The combined aqueous extracts are rendered alkaline by stirring with 800 g (10 mol) of 50% strength aqueous sodium hydroxide solution. After the stirrer has been switched off, the Hünig base separates out within a few minutes as the upper honeybrown layer. A small amount of a black organic mass which is soluble in neither the aqueous phase nor in the Hujnig base, but is soluble in acetone is formed between the two layers. The phases are separated. The recovered Hünig base contains 14% of water and can be reused without further workup.

EXAMPLE 2 (Comparative example, not according to the invention)

If the Hünig base used in Example 1 is replaced with 50% strength NaOH and the method given in Example 1 is used, the reaction mixture contains the desired product only in a yield of about 1% prior to workup.

EXAMPLE 3

Under a stream of nitrogen, 200 g of ε-caprolactam are introduced into a 1 l four-necked flask fitted with stirrer and thermometer and melted. 226 g of N,N-diisopropyl-N-ethylamine (Hünig base) and 250 g of benzoyl chloride are then added dropwise simultaneously over the course of 2 hours, with stirring. The temperature is maintained initially at 90° C.and then increased further to 110° C. When the reaction is complete, the melt, at 80° C., is introduced into 350 ml of water at room temperature and stirred. After one hour, the precipitated benzoylcaprolactam is filtered off and dried. The N-benzoylcaprolactam is obtained in a yield of 95% and a purity of >99% by GC. The Hünig base is worked up as in Example 1. The precipitated N,N-diisopropyl-N-ethylamine (water content: 0.13%) can again be reused without further purification.

EXAMPLE 4 (Comparative example, not according to the invention)

The comparison involves using soda instead of the Hünig base: 226.3 g of ε-caprolactam, 159.0 g of sodium carbonate and 1290 g of toluene are introduced into a 4 1 l flask. Under reflux, 281.1 g of benzoyl chloride are added dropwise over the course of 2 h at a rate such that $CO_2$ evolution proceeds in a controlled manner. The mixture is then refluxed for a further 4 h. The reaction mixture is cooled to room temperature using water cooling (for about 15 min.), admixed with 500 g of water and vigorously stirred, and the aqueous phase is then separated off in a separating funnel. The toluene phase that remains is evaporated in a rotary evaporator at a temperature of 60° C. and residual toluene is removed in a vacuum drying oven, giving pale oil, which crystallizes upon cooling. M.p.: 69° C. The N-benzoylcaprolactam is obtained in a yield of 88% and a purity of 98%. The $CO_2$ produced must be collected and disposed of separately.

EXAMPLE 5

In a 1 l multinecked flask fitted with stirrer, thermometer, nitrogen inlet pipe and 2 dropping funnels, 137 g of a mixture of $C_8/C_{10}$ fatty acid ethylamide (50:50) are blanketed with nitrogen and heated to 90° C. with stirring. 68 g of propionyl chloride and 111.7 g of Hünig base are then added dropwise simultaneously over the course of 1.5 h. The heat of reaction is dissipated by cooling and the temperature is maintained at 90° C. Thereafter, stirring is continued for a further 5 hours and the mixture is then cooled to room temperature. 130 ml of water are added and the mixture is stirred vigorously for half an hour, during which the Hünig base hydrochloride completely dissolves. The mixture is left to settle for half an hour and then separated from the aqueous lower phase. The upper phase is distilled under reduced pressure using a short packed column, the main fraction passing over at a head temperature of 130–152° C. (5–10 mbar). The product yield is 95% and the product purity of the resulting mixed diacylimide is 99%. The Hünig base is recovered as described in Example 1.

We claim:

1. A process for the preparation of compounds of the formula 1

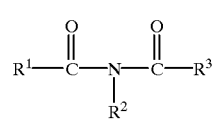

(1)

where $R^1$ and $R^2$ are $C_1$–$C_{24}$-alkyl; or $C_2$–$C_2$-alkenyl, or where $R^1$ and $R^2$ form a ring having 4 to 8 carbon atoms, and $R^3$ is $C_1$–$C_{24}$-alkyl, $C_2$–$C_{24}$-alkenyl $C_6$–$C_{14}$ -aralkyl or $C_6$–$C_{14}$-aryl which comprises reacting a secondary acid amide of the formula 2

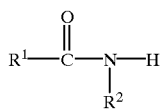
(2)

with at least one acid chloride of the formula 3

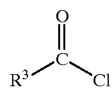
(3)

in the presence of only one basic compound N,N-diisopropyl-Nethylamine, said process is carried out without a solvent.

2. The process as claimed in claim 1, wherein $R^1$ and $R^2$ independently of one another are $C_1$–$C_{10}$-alkyl, $C_2$–$C_{10}$-alkenyl, it being possible for these radicals to be linear or branched.

3. The process as claimed in claim 1, wherein $R_2$ is methyl.

4. The process as claimed claim in 1, wherein $R^1$ and $R^2$ form a ring containing 7 atoms.

5. The process as claimed in claim 1, wherein $R^3$ is linear or branched $C_1$–$C_4$-alkyl, $C_6$–$C_{14}$-aryl or $C_6$–$C_{14}$-aralkyl.

6. The process as claimed in claim 1, wherein $R^1$ and $R^2$ together form a ring which is substituted by an $R^4$ radical, where $R^4$ is $C_1$–$C_4$-alkyl or $C_2$–$C_4$-alkenyl.

7. The process as claimed in claim 1, wherein the acid chloride and the N,N-diisopropyl-N-ethylamine are used in a molar excess of in each case up to 10%, based on the secondary amide.

8. The process as claimed in claim 1, wherein the secondary amide is initially introduced and the acid chloride and the N,N-diisopropyl-N-ethylamine are added dropwise simultaneously, the temperature being maintained at between 25 and 150° C., preferably 80 and 130° C.

9. The process as claimed in claim 1, which comprises purifying the diacylimide by adding sufficient water to dissolve the hyrochloride of the N,N-diisopropyl-N-ethylamine formed during the reaction and separating it from the diacylimide by phase separation.

10. The process of claim 8 wherein said temperature is maintained between 80° to 130° C.

11. The process of claim 1 wherein $R^3$ is benzyl or toluyl.

* * * * *